United States Patent [19]

Watanabe et al.

[11] Patent Number: 5,053,431
[45] Date of Patent: Oct. 1, 1991

[54] DERIVATIVES OF CHRYSOPHANOL AS TOPOISOMERASE II INHIBITORS

[75] Inventors: Kyoichi A. Watanabe, Rye-Brook, N.Y.; Masao Koyama, Yokohama, Japan; Ting-Chao Chou, New York, N.Y.

[73] Assignee: Sloan-Kettering Institute For Cancer Research, New York, N.Y.

[21] Appl. No.: 544,203

[22] Filed: Jun. 26, 1990

Related U.S. Application Data

[63] Continuation-in-part of Ser. No. 302,836, Jan. 27, 1989, Pat. No. 4,966,918.

[51] Int. Cl.$^5$ ............... A01N 33/02; A01N 33/10; C07C 50/18
[52] U.S. Cl. .................................. 514/649; 514/655; 514/656; 514/676
[58] Field of Search ............... 514/656, 676, 649, 655; 552/262, 266

[56] References Cited

U.S. PATENT DOCUMENTS 4,215,062 7/1980 Mitscher ..................... 552/262

OTHER PUBLICATIONS

Ventakaraman, *The Chemistry of Synthetic Dyes*, 1952, p. 83.
Barnett, *Anthracive and Anthroqunione*, 1921, pp. 174-175.

Primary Examiner—C. Warren Ivy
Assistant Examiner—Raymond Covington
Attorney, Agent, or Firm—John P. White

[57] ABSTRACT

The present invention concerns compounds of the formula:

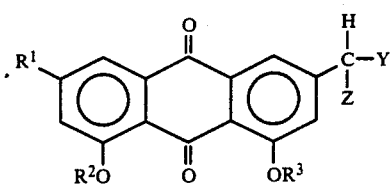

wherein
$R^1$ is hydrogen, a hydroxy group or a methoxy group;
$R^2$ is hydrogen or a methyl group;
$R^3$ is hydrogen or a methyl group;
Y is a secondary amino group (NHalkyl) or a tertiary amino group (N(alkyl)$_2$); and
Z is hydrogen or a halogen.

The invention further provides a method of inhibiting topoisomerase II using a compound having the structure:

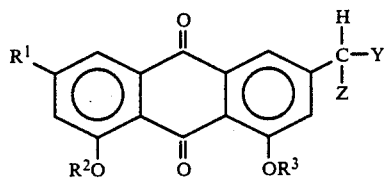

wherein
$R^1$ is hydrogen, a hydroxy group or a methoxy group;
$R^2$ is hydrogen or a methyl group;
$R^3$ is hydrogen or a methyl group;
Y is a halogen, secondary amino group (NHalkyl) or a tertiary amino group (N(alkyl)$_2$); and
Z is hydrogen or a halogen.

The invention further concerns pharmaceutical compositions which comprise the above-identified compound or the acid salts thereof, and the use of the compound or compositions for treating a malignancy in a subject.

8 Claims, 6 Drawing Sheets

FIGURE 1

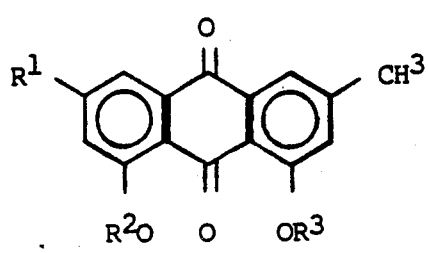

Ia    $R^1, R^2, R^3 = H$ (chrysophanol)

Ib    $R^1 = OH, R^2, R^3 = H$ (emodin)

IIa   $R^1 = H, R^2, R^3 = Me$

IIb   $R^1 = OMe, R^2, R^3 = Me$

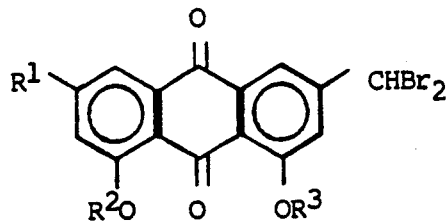

IVa   $R^1 = H, R^2, R^3 = Me$

IVb   $R^1 = OMe, R^2, R^3 = Me$

VIIa  $R^1 = H, R^2 = H(Me), R^3 = Me(H)$

VIIb  $R^1 = OMe, R^2 = H(Me), R^3 = Me(H)$

VIIIa $R^1, R^2, R^3 = H$

VIIIb $R^1 = OMe, R^2, R^3 = H$

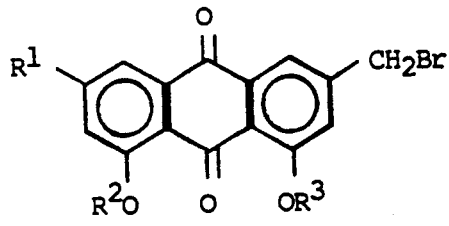

IIIa  $R^1 = H, R^2, R^3 = Me$

IIIb  $R^1 = OMe, R^2, R^3 = Me$

Va    $R^1 = H, R^2 = H(Me), R^3 = Me(H)$

Vb    $R^1 = OMe, R^2 = H(Me), R^3 = Me(H)$

VIa   $R^1, R^2, R^3 = H$

VIb   $R^1 = OMe, R^2, R^3 = H$

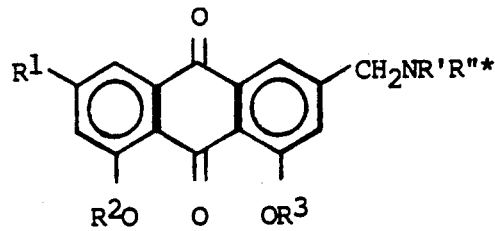

IXa   $R^1 = H, R^2, R^3 = Me$

IXb   $R^1 = OMe, R^2, R^3 = Me$

Xa    $R^1 = H, R^2 = H(Me), R^3 = Me(H)$

Xb    $R^1 = OMe, R^2 = H(Me), R^3 = Me(H)$

XIa   $R^1, R^2, R^3 = H$

XIb   $R^1 = OMe, R^2, R^3 = H$

* See Table III for NR'R"

FIGURE 3

BIOLOGICAL EFFECTS OF CHRYSOPHANOL DERIVATIVES

| COMPOUND | $R_1$ | $R_2$ | $R_3$ | $IC_{50}$ for cell growth ($\mu$m) |
|---|---|---|---|---|
| SK 31671 | -CH$_2$N(CH$_3$)$_2$ | H | H | 2.8 |
| SK 31661 | -CH$_2$N(CH$_2$-CH$_3$)$_2$ | H | H | 1.8 |
| SK 31660 | -CH$_2$N(CH$_2$CH$_2$OH)$_2$ | H | H | 3.3 |
| SK 31653 | -CH$_2$N(CH$_2$CH$_2$OH)$_2$ | H | CH$_3$ | 20.7 |
| SK 31662 | -CH$_2$N(CH$_2$CH$_2$Cl)$_2$ | H | H | 0.14 |
| SK 31669 | -CH$_2$N(pyrrolidine) | H | H | 1.14 |
| SK 31665 | -CH$_2$N(piperidine) | H | H | 2.8 |
| SK 31694 | -CH$_2$-NH-CH$_2$-CH$_2$-OH | H | H | 0.86 |
| SK 31690 | -CH$_2$-NH-CH$_2$-CH$_2$-Cl | H | H | 7.5 |
| SK 31666 | -CH$_2$Br | H | H | 7.1 |

DERIVATIVES OF CHRYSOPHANOL AS TOPOISOMERASE II INHIBITORS

The invention described herein was made in the course of work under Grant Nos. CA-08748 and CA-18856 from the National Cancer Institute, National Institutes of Health, U.S. Department of Health and Human Services. The U.S. Government has certain rights in this invention.

This application is a continuation-in-part of U.S. Ser. No. 302,836, filed Jan. 27, 1989, now U.S. Pat No. 4,966,918, the contents of which are hereby incorporated by reference into the present disclosure.

BACKGROUND OF THE INVENTION

Some of the information set forth herein has been published (see Masao Koyama, T. Ross Kelly and Kyoichi A. Watanabe, Novel Type of Potential Anticancer Agents Derived from Chrysophanol and Emodin. Some Structure-Activity Relationship Studies, [Part 1] Journal of Medicinal Chemistry, 31:283-284 (1988) which was distributed by the publisher on Jan. 29, 1988; and Masao Koyama, Kiyobumi Takahashi, Ting-Chao Chou, Zbigniew Darzynkiewicz, Jan Kapuscinski, T. Ross Kelly, and Kyoichi A. Watanabe, Intercalating Agents with Covalent Bond Forming Capability. A Novel Type of Potential Anticancer Agents. [Part 2] Derivatives of Chrysophanol and Emodin, Journal of Medicinal Chemistry, 32:1594 (1989)).

A number of analogues of certain antitumor intercalating agents, such as ellipticine (Le Pecq, J.-B., et al., Proc. Natl. Acad. Sci. U.S.A. 71:5078 (1974); Guthrie, R. W., et al., J. Med. Chem 18:755 (1975)) 4'-(9-acridinylamino) methanesulfon-m-aniside (m-AMSA, amsacrine), (Denny, W. A., et al., J. Med. Chem. 25:276 (1982)) and anthracycline antibiotics (e.g., doxorubicin) (Mosher, C. W., et al., J. Med. Chem. 25:18 (1982); Seshadri, R., et al., J. Med. Chem. 26:11 (1983); Myers, C. Cancer Chemother. 8:52 (1986)) have been synthesized in order to gain better therapeutic potential. However, preliminary screening data show that there is no straightforward structure-activity relationship within each group. These results seem to suggest that although intercalation may be a necessary condition, it may not be sufficient and other factors may be involved that per se potentiate the anticancer activity.

Studies on the mechanism of anticancer action of antibiotic CC1065 (Chidester, C. G., et al., J. Am. Chem. Soc., 103: 7629 (1981); Kanatomo, S., et al., Chem. Pharm. Bull., 29:229 (1981), Li, L. H. et al., Cancer Res. 42:999 (1982)) show that it binds to the minor groove of DNA by nonintercalative means and then slowly alkylates the amino group of adenine by opening the cyclopropane ring in the antibiotic molecule. With CC1065, covalent binding of the drug with DNA, therefore, seems to be important for its potent cytotoxic activity. Mere physical interaction between the drug and DNA may not be sufficient.

These considerations point to the development of intercalators with slow alkylating capability. Such intercalators will bind covalently and hopefully should eventually disrupt the DNA function.

The compounds of the present invention have both intercalating and alkylating functionalities, and as such are potential anticancer agents.

The compounds of this invention may also be useful as biochemical probes for biological reactions essential for DNA synthesis. Recent studies indicate that m-AMSA inhibits the topoisomerization and catenation reactions of DNA topoisomerase II (Wang, J. C. Annu. Rev. Biochem, 54:665 (1985)), probably by trapping the enzyme-DNA complexes. (Nelson, E. M., et al., Proc. Natl. Acad. Sci. U.S.A. 81:1361 (1984)); Chen, G. L., et al., J. Biol. Chem. 259:13560 (1984)). Other substances, such as etoposide (VP-16), adriamycin, and ellipticine (Kuhn, K. W., et al., Natl. Cancer Inst. Monogr. 4:61 (1987)) also stabilize the cleavable complex between DNA topoisomerase II and DNA.

In the present invention, we show that the incorporation of an alkylating group into some DNA intercalating agents greatly enhances their antileukemic properties.

SUMMARY OF THE INVENTION

The present invention concerns compounds of the formula:

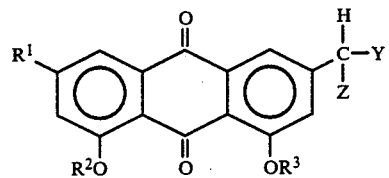

wherein
$R^1$ is hydrogen, a hydroxy group or a methoxy group;
$R^2$ is hydrogen or a methyl group;
$R^3$ is hydrogen or a methyl group;
Y is a secondary amino group (NHalkyl) or a tertiary amino group (N(alkyl)$_2$) and
Z is hydrogen or a halogen.

The invention further provides a method of inhibiting topoisomerase II using a compound having the structure:

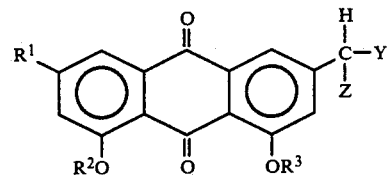

wherein
$R^1$ is hydrogen, a hydroxy group or a methoxy group;
$R^2$ is hydrogen or a methyl group;
$R^3$ is hydrogen or a methyl group;
Y is a halogen, secondary amino group (NHalkyl) or a tertiary amino group (N(alkyl)$_2$); and
Z is hydrogen or a halogen.

The invention further concerns pharmaceutical compositions which comprise the above-identified compound or the acid salts thereof, and the use of the compound or compositions for treating a malignancy in a subject.

BRIEF DESCRIPTION OF THE FIGURES

FIG. 1: Derivatives of chrysophanol and emodin.

FIG. 3: Biological effects of chrysophanol derivatives.

DETAILED DESCRIPTION OF THE INVENTION

Figure 2:
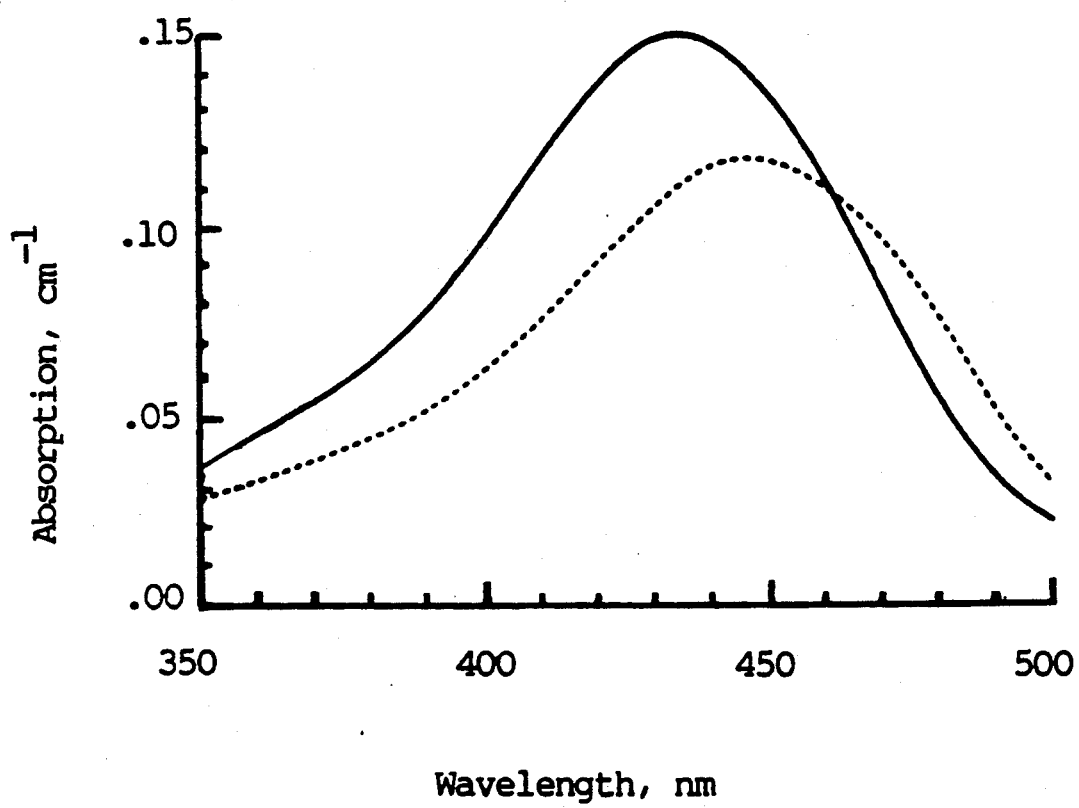
FIG. 2: Visible light absorption spectrum of derivative XIb-6 (11.3 mM in the buffer containing 0.01 M NaCl) alone (solid line) and in the presence of 0.2 mM calf thymus DNA (Sigma type 1) (broken line).
Figure 4:
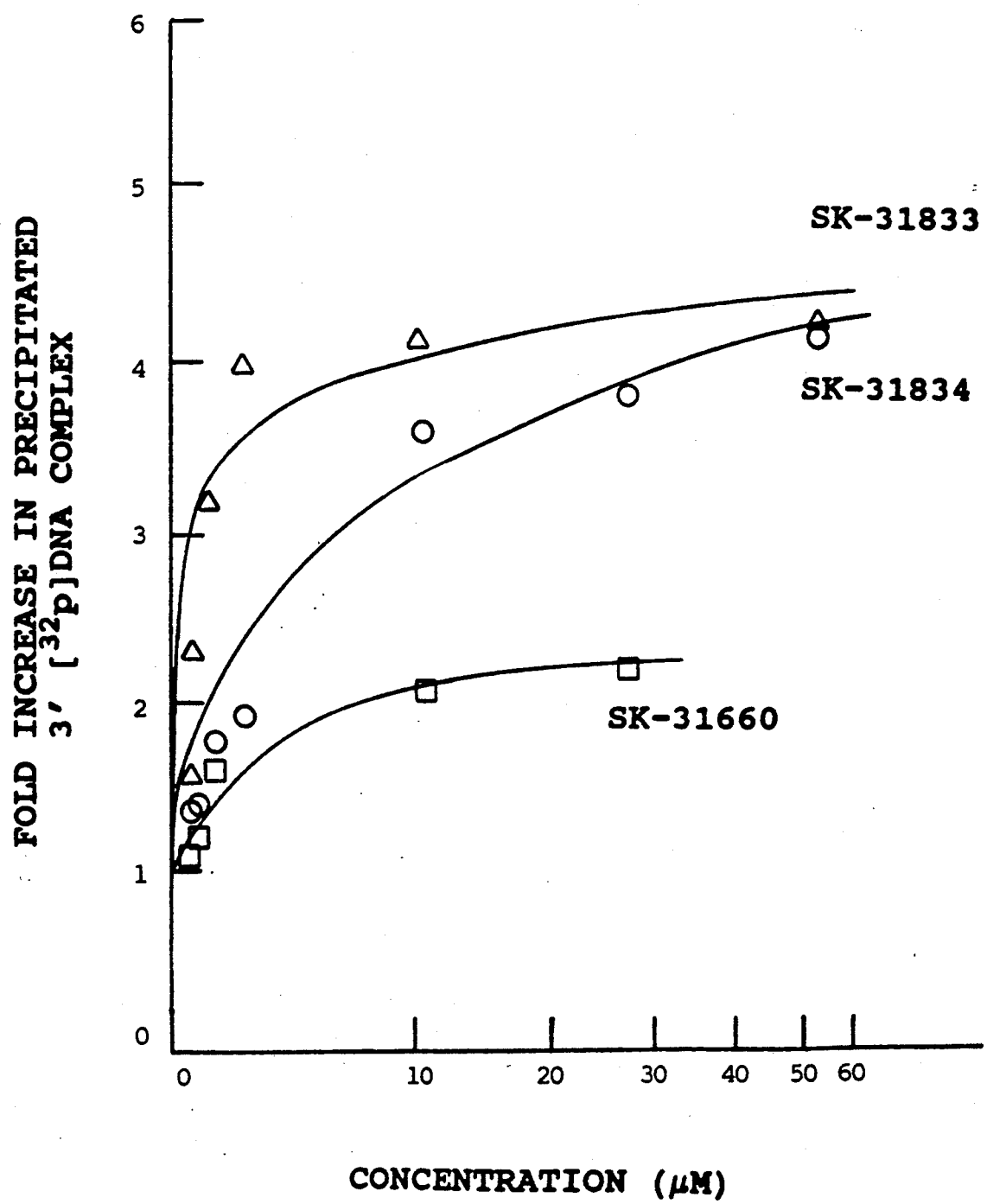
FIG. 4: Topo II cleavable complex formation. (Compounds SK-31833; SK-31824; SK-31660).
Figure 5:
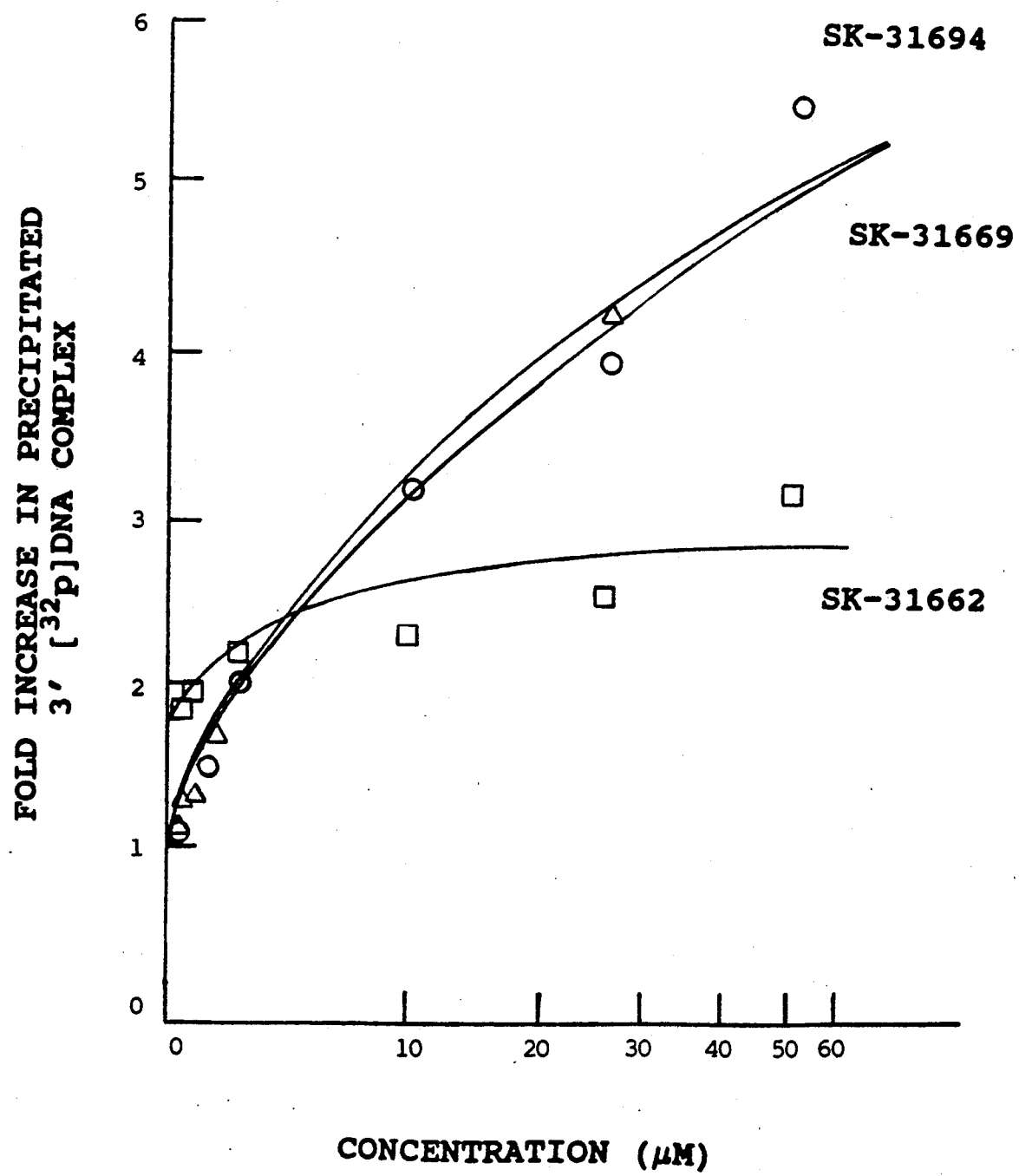
FIG. 5: Topo II cleavable complex formation. (Compounds SK-31694; SK-31669; SK-31662).
Figure 6:
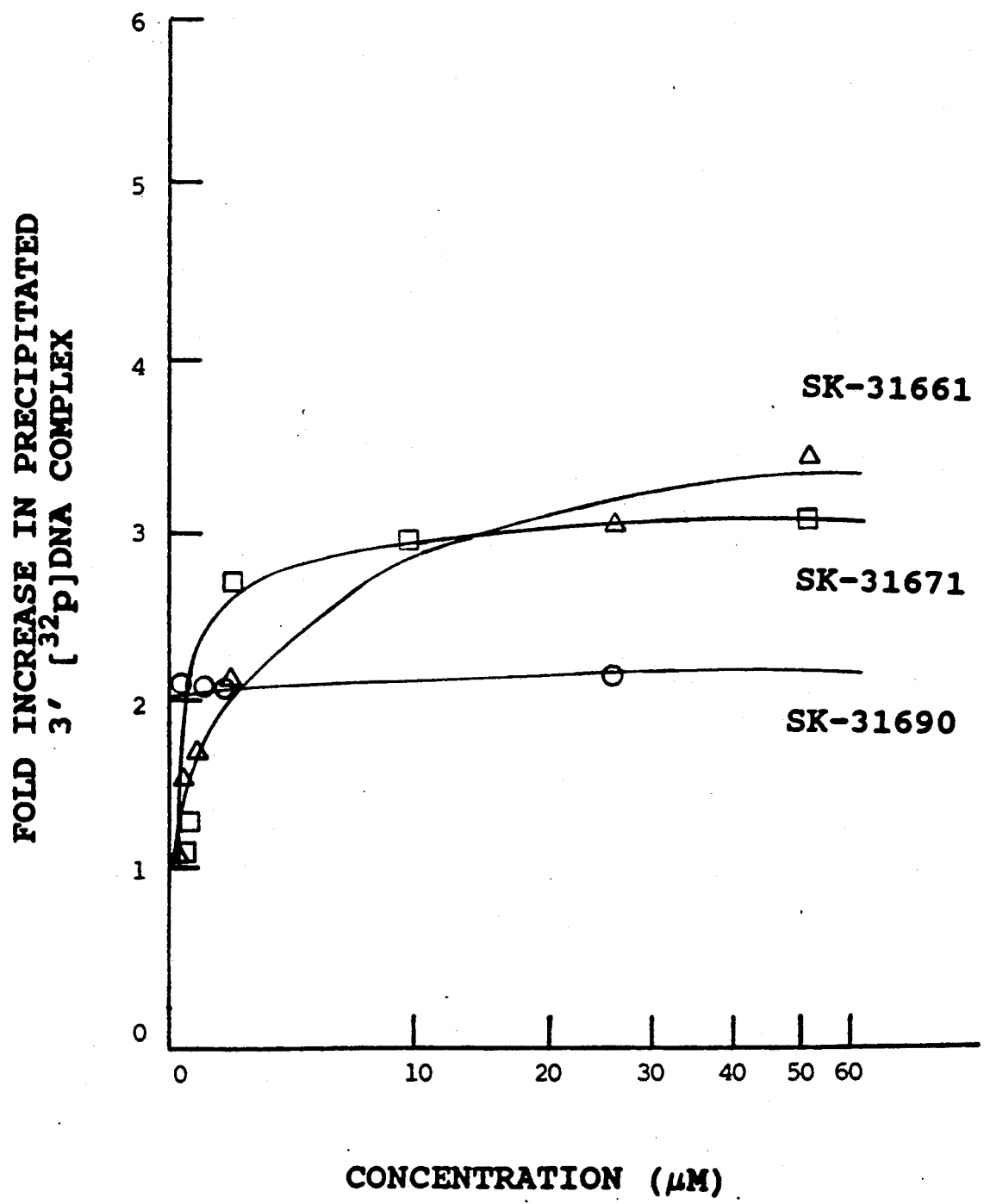
FIG. 6: Topo II cleavable complex formation. (Compounds SK-31661; SK-31671; SK-31690).

The present invention concerns compounds of the formula (I):

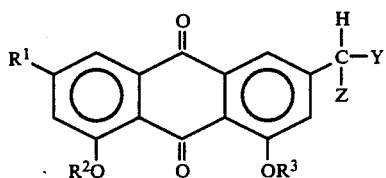

wherein
- $R^1$ is hydrogen (H), a hydroxy group (OH) or a methoxy group (OMe);
- $R^2$ is hydrogen or a methyl group (Me);
- $R^3$ is hydrogen or a methyl group;
- Y is a secondary amino group (NHalkyl) or a tertiary amino group (N(alkyl)$_2$) and
- Z is hydrogen or a halogen.

When Y is a secondary amino group, e.g. (-NHalkyl), or a tertiary amino group, e.g. (-N(alkyl)$_2$), it is preferred that the alkyl groups be lower alkyl groups, e.g. groups having from one to about five carton atoms. Particularly effective are methyl or ethyl groups. The lower alkyl groups may also have substituents on the carbon atoms for the hydrogens. The alkyl groups may be substituted with one or more hydroxyl group(s), for example 2-hydroxyethyl, or formed into organic acyl esters, such as acetyl, benzoyl or methanesulfonyl esters, i.e. the substituents are benzoxy, acetyloxy, or methylsulfonyloxy. Further, the alkyl groups may be substituted with halogen(s), such as chlorine and/or bromine to form groups such as a 2-chloroethyl or a 2-bromoethyl.

The invention also provides a method of inhibiting topoisomerase II using the compound of claim 1.

The invention further provides a method of inhibiting topoisomerase II using a compound having the structure:

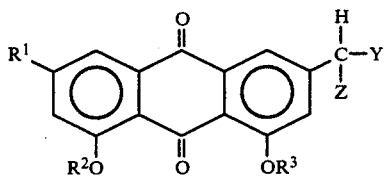

wherein
- $R^1$ is hydrogen, a hydroxy group or a methoxy group;
- $R^2$ is hydrogen or a methyl group;
- $R^3$ is hydrogen or a methyl group;
- Y is a halogen, secondary amino group (NHalkyl) or a tertiary amino group (N(alkyl)z); and
- Z is hydrogen or a halogen.

The halogen may be chlorine or bromine. The secondary amino group preferably comprises a lower alkyl group or a substituted lower alkyl group where each substituent is a halogen or a hydroxy, benzoxy, or acetyloxy group. The tertiary amino group preferably comprises two lower alkyl groups or substituted lower alkyl groups where each substituent is a halogen or a hydroxy, benzoxy, or acetyloxy group and where the lower alkyl groups or the substituted lower alkyl groups are the same or different.

The invention also provides for pharmaceutical compositions for the treatment of a malignancy in a subject comprising the compound or a pharmaceutically acceptable acid salt thereof, and a pharmaceutically acceptable carrier, the amount of the composition being an amount effective to suppress the growth of the malignancy, preferably from 1-200 mg/kg of the body weight of the subject.

The invention further provides for a method of treating a subject having a malignancy which comprises administering to the subject an effective amount of the compound to suppress the growth of the malignancy. A subject may be any warmblooded animal, preferably human. The malignancy is preferably a tumor or leukemia.

The following Experimental Detail Section and Examples are set forth to aid in an understanding of the invention. These sections are not intended to, and should not be construed to, limit in any way the invention set forth in the claims which follow thereafter.

EXPERIMENTAL DETAIL

The present invention provides a novel class of compounds, anthraquinones, which possess covalent bonding capability. Such compounds may intercalate into DNA and then bind covalently to DNA, thereby exerting cytotoxic activity.

EXPERIMENT 1

The starting materials for the compounds of the present experiment are of the formula II:

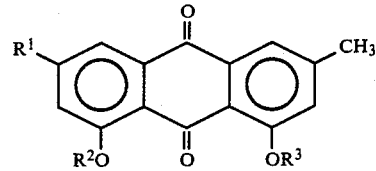

Typical examples contain the following combinations of $R^1$, $R^2$, and $R^3$.

|     | $R^1$ | $R^2$ and $R^3$ |             |
| --- | ----- | --------------- | ----------- |
| IIa | H     | H               | chrysophanol |
| IIb | OH    | H               | emodin      |
| IIc | H     | Me              |             |
| IId | OMe   | H               |             |
| IIe | OMe   | Me              |             |

Compounds IIc-IIe are known, and can be prepared readily from the natural product, chrysophanol or emodin (IIa or IIb), by the known procedures.

Compounds of formula II are treated with N-bromosuccinimide (NBS) or 1,3-dibromo-5,5-dimethylhydantoin (BMH) in a halogenated hydrocarbon, preferably carbon tetrachloride, in the presence of a peroxide, such as m-chloroperbenzoic acid or benzoyl peroxide to give the corresponding monobromides of the formula III as the major products and dibromides of formula IV as the minor products:

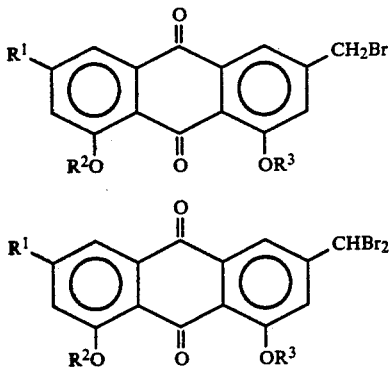

III

IV

The reaction is carried out at a temperature range of from 25° C. to 100° C., preferably at the boiling temperature of the solvent (77° C. for carbon tetrachloride) in a period from one hour to three days. The molar ratio of the reactants, formula II to NBS or BMH, can be from 1:1 to 1:3, preferably 1:1.2. Upon completion of the reaction, insoluble materials are removed by filtration, the filtrate concentrated, and the residue recrystallized to give formula III compounds. From the mother formula, IV compounds can be obtained after chromatography on a silica gel column.

The 1,8-dimethoxy derivatives IIIc, IIIe, IVc and IVe can be converted into the corresponding 1,8-dihydroxy derivatives IIIa, IIId, IVa, and IVd, respectively, by treatment with hydrogen bromide in acetic acid.

Treatment of compounds of formula III with a primary or secondary amine with or without solvent affords corresponding products of formula V:

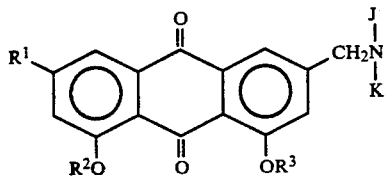

V

Some of the typical examples contain the following combinations of $R^1$, $R^2$, $R^3$, J and K.

| V | $R^1$ | $R^2$ and $R^3$ | J | K |
|---|---|---|---|---|
| Va | H | H | Et | Et |
| Vb | H | H | $CH_2CH_2OH$ | $CH_2CH_2OH$ |
| Vc | H | H | Et | H |
| Vd | H | H | $CH_2CH_2OH$ | H |
| Ve | OMe | H | Et | Et |
| Vf | OMe | H | $CH_2CH_2OH$ | $CH_2CH_2OH$ |
| Vg | OMe | H | Et | H |
| Vh | OMe | H | $CH_2CH_2OH$ | H |
| Vi | H | Me | Et | Et |
| Vj | H | Me | $CH_2CH_2OH$ | $CH_2CH_2OH$ |
| Vk | H | Me | Et | H |
| Vl | H | Me | $CH_2CH_2OH$ | H |
| Vm | OMe | Me | Et | Et |
| Vn | OMe | Me | $CH_2CH_2OH$ | $CH_2CH_2OH$ |
| Vo | OMe | Me | Et | H |
| Vp | OMe | Me | $CH_2CH_2OH$ | H |

The 1,8-dimethoxy derivatives of formula V (Vi-Vp) can be converted into their corresponding 1,8-dihydroxyanthraquinones of formula V (Va-Vh) by treatment with hydrogen bromide in acetic acid.

The 2-hydroxyethylamino derivatives (Vb, Vd, Vf, Vh, Vj, Vl, Vn and Vp) can be further converted into their corresponding 2-chloroethyl derivatives (Vq-Vx) by treatment with a conventional chlorinating agent, such as thionyl chloride, sulfonyl chloride, phosphorus oxychloride or carbon tetrachloride and triphenylphosphine.

| V | $R^1$ | $R^2$ and $R^3$ | J | K |
|---|---|---|---|---|
| Vq | H | H | $CH_2CH_2Cl$ | $CH_2CH_2Cl$ |
| Vr | H | H | $CH_2CH_2Cl$ | H |
| Vs | OMe | H | $CH_2CH_2Cl$ | $CH_2CH_2Cl$ |
| Vt | OMe | H | $CH_2CH_2Cl$ | H |
| Vu | H | Me | $CH_2CH_2Cl$ | $CH_2CH_2Cl$ |
| Vv | H | Me | $CH_2CH_2Cl$ | H |
| Vw | OMe | Me | $CH_2CH_2Cl$ | $CH_2CH_2Cl$ |
| Vx | OMe | Me | $CH_2CH_2Cl$ | H |

The reaction is carried out at a temperature range of from 0° C. to 100° C., preferably at room temperature, in a period from half an hour to eight hours, in a solvent such as N,N-dimethylformamide, N,N-dimethylacetamide, diethyl ether or tetrahydrofuran, preferably in N,N-dimethylformamide.

In a similar manner, the corresponding 2-bromoethyl derivatives can be obtained by bromination of the 2-hydroxyethyl intermediates with thionyl bromide, phosphorus oxybromide or carbon tetrabromide and triphenylphosphine in N,N-dimethylformamide.

Acylation of the 2-hydroxyethyl intermediates with acid anhydride, such as acetic anhydride, benzoic anhydride or methanesulfonic anhydride, or with acyl chloride, such as acetyl chloride, benzoyl chloride or methanesulfonyl chloride, in pyridine or in a mixture of chloroform and p-dimethylaminopyridine or methylenechloride and p-dimethylaminopyridine, affords the corresponding acyl derivatives.

The following examples are illustrative of the process and the products of the present experiment, but are not to be construed as limiting.

EXAMPLE 1

To a hot solution of 1,8-dimethoxy-3-methyl-9,10-anthraquinone (4.5 g, 16 mM) and 1,3-dibromo-5,5-dimethylhydantoin (2.75 g, 19.2 mM) in carbon tetrachloride (500 mL) is added benzoyl peroxide (0.7 g), and the mixture is heated under reflux for 5 hours. The mixture is allowed to cool to room temperature. Insoluble hydantoin is removed by filtration, the filtrate is concentrated to dryness, and the residue recrystallized twice from ethyl acetate to give 3-bromomethyl-1,8-dimethoxy-9,10-anthraquinone(3.3 g, 57%), mp 176–178° C. $^1$H NMR (CDCl$_3$)δ: 4.01 (3H, s, OMe), 4.03 (3H, s, OMe), 4.52 (2H, s, CH$_2$Br), 7.26–7.84 (5H, m, aromatic H). Analyses ($C_{17}H_{13}BrO_4$) Calculated: C, 56.53; H, 3.63; Br, 22.12. Found: C, 56.48; H, 3.67; Br, 21.93.

The mother liquors of recrystallization of above are concentrated, and the residue chromatographed on a silica gel column using a mixture of benzene and ethyl acetate. 3-Dibromomethyl-1,8-dimethoxy-9,10-anthraquinone (0.48 g) is eluted form the column followed by 3-bromomethyl-1,8-dimethoxy-9,10-anthraquinone (0.33 g). The former has the following characteristics: mp 207–210° C., $^1$H NMR (CDCl$_3$)δ: 4.01 (3H, s, OMe), 4.07 (3H, s, OMe), 6.67 (1H, s, CHBr$_2$), 7.26–7.92 (5H, m, aromatic H). Analyses ($C_{17}H_{12}Br_2O_4$) Calculated: C, 46.40; H, 2.75; Br, 36.31. Found: C, 46.63; H, 2.87; Br, 36.23.

Following the same procedure but using the corresponding anthraquinones as the starting materials, the following 3-bromomethyl- and 3,3-dibromomethyl-9,10-anthraquinones are prepared: 3-bromomethyl-1,6,8-trimethoxy-9,10-anthraquinone, 3,3-dibromomethyl-1,6,8-trimethoxy-9,10-anthraquinone, 3-bromomethyl-1,8-dihydroxy-9,10-anthraquinone, 3,3-dibromomethyl-1,8-dihydroxy-9,10-anthraquinone, 3-bromomethyl-1,6,8-trihydroxy-9,10-anthraquinone, 3,3-dibromomethyl-1,6,8-trihydroxy-9,10-anthraquinone, 3-bromomethyl-1,8-dihydroxy-6-methoxy-9,10-anthraquinone, 3,3-dibromomethyl-1,8-dihydroxy-6-methoxy-9,10anthraquinone By the following the same procedure, but using N-bromosuccinimide instead of 3,3-dibromo-5,5-dimethylhydantoin, the same products above are prepared from their corresponding 3-methyl-9,10-anthraquinone starting materials.

EXAMPLE 2

A mixture of 3-bromomethyl-1,8-dimethoxy-9,10-anthraquinone (1.05 g), 30% hydrogen bromide in acetic acid (5 mL) and acetic acid (50 mL) is heated at 100° C. for 5 hours. After cooling the mixture, 3-bromomethyl-1,8-dihydroxy-9,10-anthraquinone is collected by filtration, washed with acetic acid, and then air-dried to give 879 mg (91%) of the product, mp 220-222° C. $^1$H NMR (CDCl$_3$) 4.47 (2H, s, CH$_2$Br), 7.27–7.91 (5H, m, aromatic H), 12.02 (1H, s, OH), 12.05 (1H, s, OH). Analyses (C$_{15}$H$_9$BrO$_4$). Calculated: C, 54.08; H, 2.71; Br, 23.99. Found: C, 54.00; H, 2.92; Br, 24.16.

By following the same procedure but using the corresponding 1,8-dimethoxy-9,10-anthraquinones, the following compounds are prepared:

3,3-dibromomethyl-1,8-dihydroxy-9,10-anthraquinone, 3-bromomethyl-1,8-dihydroxy-6-methoxy-9,10-anthraquinone, 3,3-dibromomethyl-1,8-dihydroxy-6-methoxy-9,10-anthraquinone.

EXAMPLE 3

A mixture of 3-bromomethyl-1,8-dihydroxy-9,10-anthraquinone (456 mg) and bis(2-hydroxyethyl)amine (600 mg) in N,N-dimethylformamide (20 mL) is stirred for 2 hours, and then partitioned between chloroform (100 mL) and water (100 mL). The organic layer is separated, washed with water (50 mL× 3), dried over sodium sulfate, and then concentrated to dryness. The residue is chromatographed on a silica gel column using chloroform-methanol (15:1 v/v) as the eluent. Upon concentration of the major fraction, 3-[N,N-bis(2-hydroxyethyl)amino] methyl-1,8-dihydroxy-9,10-anthraquinone is obtained as a solid: $^1$H NMR (CDCl$_3$)δ: 2.77 (4H, t, NCH$_2$CH$_2$O), 3.78 (4H, t, NCH$_2$CH$_2$O), 4.78 (2H, s, CH$_2$N=), 7.21–7.29 (5H, m, aromatic H), 11.95 (1H, s, OH), 12.00 (1H, s, OH).

The solid is dissolved in 1N hydrochloric acid, and the solvent is removed in vacuo. The crystalline hydrochloride salt (495 mg, 91%) is triturated with methanol (5 mL), mp 204–207° C. (decomposition). Analyses (C$_1$H$_{19}$NO$_6$·HCl). Calculated: C, 57.95; H, 5.12; N, 3.56. Found: C, 58.00; H, 5.26; N, 3.37.

By following the same procedure but using the corresponding 3-bromomethyl-9,10-anthraquinones, the following compounds and their hydrochloric acid salts are prepared:

3-[N,N-diethylamino)methyl-1,8-dihydroxy-9,10-anthraquinone,
3-[N-ethylamino)methyl-1,8-dihydroxy-9,10-anthraquinone,
3-[N-(2-hydroxyethyl)amino]methyl-1,8-dihydroxy-9,10-anthraquinone,
3-(N,N-diethylamino)methyl-1,8-dihydroxy-6-methoxy-9,10-anthraquinone,
3-[N,N-bis(2-hydroxyethyl)amino]methyl-1,8-dihydroxy-6-methoxy-9,10-anthraquinone,
3-(N-ethylamino)methyl-1,8-dihydroxy-6-methoxy-9,10-anthraquinone,
3-[N-(2-hydroxyethyl)amino]methyl-1,8-dihydroxy-6-methoxy-9,10-anthraquinone,
3-(N,N-diethylamino) methyl-1,8-dimethoxy-9,10-anthraquinone,
3-[N,N-bis(2-hydroxethyl)amino]methyl-1,8-dimethoxy-9,10-anthraquinone,
3-(N-ethylamino)methyl-1,8-dimethoxy-9,10-anthraquinone,
3-[N-(2-hydroxyethyl)amino]methyl-1,8-dimethoxy-9,10-anthraquinone,
3-(N,N-diethylamino)methyl-1,6,8-trimethoxy-9,10-anthraquinone,
3-[N,N-bis(2-hydroxethyl)amino]methyl-1,6,8-trimethoxy-9,10-anthraquinone,
3-(N-ethylamino)methyl-1,6,8-trimethoxy-9,10-anthraquinone,
3-[N-(2-hydroxyethyl)amino]methyl-1,6,8-trimethoxy-9,10-anthraquinone,

EXAMPLE 4

To a solution of 3-[N,N-bis(2-hydroxyethyl)amino]-methyl-1,8-dihydroxy-9,10-anthraquinone, (162 mg) in dry N,N-dimethylformamide (5 mL) is added thionyl chloride (0.2 mL). After 2 hours at room temperature, the mixture is concentrated in vacuo to dryness, and the residue is triturated well with methanol (3 mL). 3-[N,N-Bis(2-chloroethyl) aminomethyl-1,8-dihydroxy-9,10-anthraquinone that is crystallized is collected by filtration, 172 mg (96%), mp 211–214° C. (decomposition). $^1$H NMR (CDCl$_3$)δ: 3.48 (4H, t, NCH$_2$CH$_2$Cl), 3.85 (4H, t, NCH$_2$CH$_2$Cl), 4.34 (2H, d, CH$_2$N=), 7.32–7.95 (5H, m, aromatic H). Analyses (C$_{19}$H$_{17}$Cl$_2$NO$_4$·HCl). Calculated: C, 52.98; H, 4.21; Cl, 24.24; N, 3.25. Found: C, 52.79; H, 4.32; Cl, 24.41; N, 3.36.

By following the same procedure but using the corresponding (2-hydroxyethyl)amino derivatives, the following compounds are prepared:
3-[N-(2-chloroethyl)amino]methyl-1,8-dihydroxy-9,10-anthraquinone,
3-[N,N-bis(2-chloroethyl)amino]methyl-1,8-dihydroxy-6-methoxy-9,10-anthraquinone,
3-[N-(2-chloroethyl)amino]methyl-1,8-dihydroxy-6-methoxy-9,10-anthraquinone,
3-[N,N-bis(2-chloroethyl)amino]methyl-1,8-dimethoxy-9,10-anthraquinone,
3-[N-(2-chloroethyl)amino]methyl-1,8-dimethoxy-9,10-anthraquinone,
3-[N,N-bis(2-chloroethyl)amino]methyl-1,8,6-trimethoxy-9,10-anthraquinone.
3-[N-(2-chloroethyl)amino]methyl-1,6,8-trimethoxy-9,10-anthraquinone.

EXPERIMENTAL DISCUSSION

Table I list typical results supporting the use of the present compounds as anti-cancer agents in the treatment of subjects.

TABLE I

Inhibitory activity of some 9,10-anthraquinone derivatives.

| Compounds | melting point (°C.) | ID$_{50}$ (μg/mL) | ID$_{50}$ (μM) |
|---|---|---|---|
| IIa | 194–195 | >100 | >390 |
| IIb | 256–257 | >100 | >335 |
| Va (HCl) | 235–238 (dec) | 0.99 | 2.8 |
| Vb (HCl) | 204–207 (dec) | 2.33 | 5.9 |
| Vc (HCl) | >275 | 0.26 | 0.77 |
| Vd (HCl) | 255–261 (dec) | 0.066 | 0.16 |
| Ve (HBr) | 240–241 (dec) | 0.51 | 1.16 |
| Vf (HCl) | 225–227 (dec) | 5.80 | 13.7 |
| Vg (HBr) | >275 | 0.18 | 0.44 |
| Vh (CHc) | 259–260 (dec) | 0.072 | 0.19 |
| Vi (HCl) | 154–158 | 52.3 | 128.3 |
| Vj (HCl) | 202–205 (dec) | >21 | >49.8 |
| Vk (HCl) | 254–255 (dec) | 1.30 | 3.59 |
| Vl (HCl) | 251–252 (dec) | 53.7 | 142.0 |
| Vm (HCl) | 222–223 (dec) | 2.90 | 6.91 |
| Vn (HCl) | 226–227 (dec) | 12.5 | 27.7 |
| Vo (HCl) | 267–269 (dec) | 1.44 | 3.67 |
| Vp (HCl) | 252–253 (dec) | 5.10 | 12.5 |
| Vq (HCl) | 211–214 (dec) | 0.058 | 0.13 |
| Vr (HCl) | 255–261 (dec) | 2.37 | 7.11 |
| Vs (HCl) | 203–206 (dec) | 0.010 | 0.023 |
| Vu (HCl) | 208–209 (dec) | 5.73 | 12.5 |
| Vw (HCl) | 200–201 (dec) | 1.30 | 2.66 |

The starting materials, chrysophanol and emodin (IIa and IIb), are capable of intercalating into DNA but do not possess covalent bond forming capability, and exhibit little anticancer activity. The 1,8-dimethoxy intermediates (Vu-Vx), that bear alkylating potential but are incapable of intercalating into DNA due to the presence of bulky methoxy groups, are active only to a small extent against mouse leukemia L1210 cells. Those compounds that are capable of intercalating into DNA and bind covalently to the DNA after intercalation (Vq-Vt) do exhibit extremely potent activity against L1210 cells.

Table II lists additional results supporting the anticancer use of the present experiment.

TABLE II

Antileukemic activity of chrysophanol derivatives bearing alkylating potential.

| J and K | R$^1$ | R$^2$ | R$^3$ | L1210: ID$_{50}$, μM |
|---|---|---|---|---|
| Et | H | Me | Me | 128.3 |
| Et | H | H (or Me) | Me (or H) | 11.9 |
| Et | H | H | H | 2.75 |
| CH$_2$CH$_2$OH | H | Me | Me | >50 |
| CH$_2$CH$_2$OH | H | H (or Me) | Me (or H) | 23.4 |
| CH$_2$CH$_2$OH | H | H | H | 5.92 |
| CH$_2$CH$_2$Cl | H | Me | Me | 12.5 |
| CH$_2$CH$_2$Cl | H | H (or Me) | Me (or H) | 1.40 |
| CH$_2$CH$_2$Cl | H | H | H | 0.13 |
| Et | OMe | Me | Me | 6.91 |
| Et | OMe | H | H | 1.16 |
| CH$_2$CH$_2$OH | OMe | Me | Me | >27.6 |
| CH$_2$CH$_2$OH | OMe | H | H | 13.7 |
| CH$_2$CH$_2$Cl | OMe | Me | Me | 2.66 |
| CH$_2$CH$_2$Cl | OMe | H (or Me) | Me (or H) | 1.75 |
| CH$_2$CH$_2$Cl | OMe | H | H | 0.023 |

3-[N,N-Bis(2-chloroethyl)amino]methyl-1,8-dihydroxy-9/10-anthraquinone (Vq) is extremely potent against mouse leukemia L1210 made resistant to Cisplatin. At the dosage of 100 mg/kg/day × 5 (ip), mice inoculated with Cisplatin resistant leukemia L1210/Cisplatin are cured.

The process of treating tumors according to this invention comprises administering to a subject having an abnormal proportion of leukocytes or other evidence of a malignancy, a therapeutic nontoxic amount of a compound of the experiment such as 3-[N,N-Bis(2-chloroethyl)amino]methyl-1,8-dihydroxy-9,10-anthraquinone, as such or in the form of a pharmaceutically acceptable salt thereof. The invention also provides a pharmaceutical composition in dosage unit form comprising from 1 to 200 mg/kg of a compound of the invention, per dosage unit, together with pharmaceutically acceptable nontoxic inert carrier or diluent thereof as described above. A subject may be any warm-blooded animal and is preferably human.

EXPERIMENT 2

Fifty-one new C-methyl-modified derivatives of the anthraquinones chrysophanol and emodin or their various methyl ethers were prepared for structure-activity relationship studies of anticancer activity against mouse leukemia L1210 and human leukemia HL-60 cells. Representative compounds were spectrophotometrically studied for their capacity to interact with natural and denatured DNA. In general, those anthraquinones bearing an amino function interact with DNA. 1,8-Dimethoxyanthraquinones are incapable of intercalating into DNA. 1- or 8-Monohydroxy-monomethoxyanthraquinones, however, interact with DNA to some extent. No straightforward correlation is apparent between the DNA-affinity data of the compounds studied spectrophotometrically and their cytotoxic effects. Cytotoxic potencies of these compounds on cell growth inhibition during a 72-h period are inversely correlated to their potencies when inhibiting [$^3$H]TdR incorporation into DNA during the initial 30 min of exposure. Surprisingly, some compounds that showed more cytotoxicity did not inhibit initial TdR incorporation (0–30 min), while some others that strongly inhibited TdR incorporation initially did not exhibit cytotoxicity in 72 h. The results suggest that the cytotoxicity produced by these compounds is time dependent and is not a direct result of initial inhibition of DNA replication.

It is well-known that one the of the metabolites of ellipticine, 9-hydroxyellipticine (Lesca, P., et al., Biochem. Pharmacol. 26:2169 (1977)) (9-OH-E), is also a potent anticancer agent. (Le Pecq, J.-B.; Cancer Res. 36:3067 (1976))2-N-Methyl-9-hydroxyellipticinium (9-OH-NME) is one of the most active drugs among the ellipticine analogues (Bernadou, J. Proc. Natl. Acad. Sci. U.S.A. 81:1297 (1984)). The latter is easily oxidized by peroxidases to 9-oxo-2-methylellipticinium (Auclair, C., et al., J. Med. Chem. 24:289 (1981); Eernadou, J., et al., J. Med. Chem. 26:574 (1983)) (9-oxo-NME), which is highly electrophilic and alkylates various nitrogen, (Meunier, G.; Tetrahedron Lett. 26:574 (1983); Auclair, C.; J. Med. Chem. 27:1161 (1984)) sulfur, (Monsarrat, B.; Biochem. Pharmacol. 32:3887 (1983)) and oxygen (Bernadou, J., et al., J. Med. Chem. 26:574 (1983); Meunier, G., et al., Tetrahedron Lett. 26:574 (1983)) nucleophiles. Among biological macromolecules, proteins, (Auclair, C., et al., Biochem. Pharmacol. 32:3883 (1984) polyadenylate, (Dugue, B., et al., Biochem. Biophys. Res. Commun. 124:416 (1984)) RNA, (Dugue, B., et al.) and DNA (Auclair, C., et al., Biochemistry 25:1240 (1986) are easily alkylated by 9-oxo-NME. This "biooxidative alkylation" has been proposed as a possible mode of anticancer action. (Dugue, B., et al., Cancer Res. 46:3828 (1986).

For other intercalating anticancer agents, such as amsacrine (m-AMSA), and the anthracycline antibiotics, extensive studies on their mechanism of anticancer action (Nelson, E. M., et al., Proc. Natl. Acad. Sci.

U.S.A. 81:1361 (1984); Chen, G. L., et al., J. Biol. Chem. 259:13560 (1984); Riou, J. F., et al., Biochem. Pharmacol. 35:4409 (1986); Crooke, S. T., Reich, S. D.; Eds Anthracyclines: Current Status and New Developments; Academic Press: New York, (1980); Myers, C. E. In Pharmacologic Principles of Cancer Treatment; Chabner, B., Ed.; Saunders: Philadelphia p. 416 (1982); DiMarco, A. In Cancer Medicine; Holland, J. F., Frei, E. Eds; Lea and Febiger: Philadelphia, 2nd ed., p. 872 (1982); Muggia, F. M., Young, C. W., Carter, S. K. Eds. Anthracycline Antibiotics in Cancer Therapy; Martinus Nijhoff: Hague/Boston/New York, pp. 71–174 (1982)) and QSAR studies directed toward the development of more selective drugs have been conducted. (Ferguson, L. R., Denny, W. A., J. Med. Chem. 23:269 (1980); Denny, W. A., et al., J. Med. Chem. 25:276 (1982); Alexander, J., et al., J. Med. Chem. 27:1343 (1984)). Whether these intercalators bind covalently to biomolecules has not been established.

In order to test our hypothesis that intercalating agents with covalent bond forming capability may exert potent cytocidal activity, we chose chrysophanol Ia and emodin Ib (FIG. 1) as the starting materials; Ia and Ib were isolated from crude rhubarb extract. (Kelly, T. R.; J. Org. Chem. 48:3573 (1983)). Both compounds exhibit little anticancer or cytocidal activity. Their structural aromatic features indicate that these compounds and their derivatives (particularly positively charged ones) may intercalate into double helix of nucleic acids.

CHEMISTRY

The hydroxy groups at the 1- and 8-positions of I were methylated with methyl sulfate and $K_2CO_3$ in acetone (Alexander, J., et al., J. Org. Chem. 45:20 (1980)) to the known 1,8-dimethoxy-9,10-anthraquinones II. The C-methyl group of II was then brominated with NBS (Banvill, J., et al., J. Chem Soc. Perkin Trans. I, 613 (1976)) or 1,3-dibromo-5,5-dimethylhydantoin (BDH) (Sargent, M. V., et al., J. Chem. Soc., C 2763 (1969); Cava, M. P., et al., Tetrahedron 40:4767 (1984)) in carbon tetrachloride in the presence of benzoyl peroxide to give monobromide III as the major product along with a small amount of dibromide IV. Treatment of III with various amines including mono(2-hydroxyethyl)amine and bis(2-hydroxyethyl)amine afforded the corresponding alkyl-amino derivatives IX (Table III). Chlorination of the (2-hydroxyethyl)amino derivatives IX-2 gave the corresponding 3-[[(2-chloroethyl)amino]methyl]9,10-anthraquinones IX-3. On the basis of reports by Anderson et al. (Anderson, W. K., et al., J. Med. Chem. 20:812 (1977); Anderson, W. K., et al., J. Med. Chem. 22:977 (1979); Anderson, W. K., et al., J. Med. Chem. 26:1333 (1983); Zwelling, L. A. Cancer Metastasis Rev. 4:263 (1985)) that certain carbamates are susceptible to nucleophilic attack, we synthesized N-methylcarbamate IX-4 by treatment of IX-2 with N-methyl isocyanate.

TABLE III

Synthetic Derivatives of Chrysophanol and Emodin

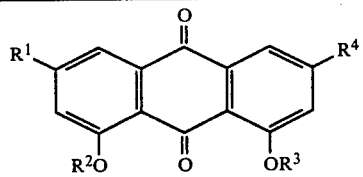

| compd[a] | R[1] | R[2] | R[3] | R[4] | mp, °C.[b,c] | formula |
|---|---|---|---|---|---|---|
| IIa | H | Me | Me | Me | 189–190 | $C_{17}H_{14}O_4$ |
| IIb | OMe | Me | Me | Me | 228–229 | $C_{18}H_{16}O_5$ |
| IIIa | H | Me | Me | $CH_2Br$ | 176–178 | $C_{17}H_{13}BrO_4$ |
| IIIb | OMe | Me | Me | $CH_2Br$ | 250–254 | $C_{18}H_{15}BrO_5$ |
| IVa | H | Me | Me | $CHBr_2$ | 207–210 | $C_{17}H_{12}Br_2O_4$ |
| IVb | OMe | Me | Me | $CHBr_2$ | 254–257 | $C_{17}H_{14}Br_2O_5$ |
| Va | H | H or Me | Me or H | $CH_2Br$ | 213–215 | $C_{16}H_{11}BrO_4$ |
| Vb | OMe | H or Me | Me or H | $CH_2Br$ | 199–201 | $C_{17}H_{13}BrO_5$ |
| VIa | H | H | H | $CH_2Br$ | 220–222 | $C_{15}H_9BrO_4$ |
| VIb | OMe | H | H | $CH_2Br$ | 249–250 | $C_{16}H_{11}BrO_5$ |
| VIIa | H | H or Me | Me or H | $CHBr_2$ | 176–178 | $C_{16}H_{10}Br_2O_4$ |
| VIIb | OMe | H or Me | Me or H | $CHBr_2$ | 202–203 | $C_{17}H_{12}Br_2O_5$ |
| VIIIa | H | H | H | $CHBr_2$ | 211–213 | $C_{15}H_8Br_2O_4$ |
| VIIIb | OMe | H | H | $CHBr_2$ | 237–238 | $C_{16}H_{10}Br_2O_5$ |
| IXa-1 | H | Me | Me | $CH_2NEt_2$ | 154–158 | $C_{21}H_{23}NO_4.HCl.H_2O$ |
| Ixa-2 | H | Me | Me | $CH_2N(CH_2CH_2OH)_2$ | 202–205d | $C_{21}H_{23}NO_6.HCl$ |
| IXa-3 | H | Me | Me | $CH_2N(CH_2CH_2Cl)_2$ | 205–206d | $C_{21}H_{21}Cl_2NO_4.HCl$ |
| IXa-4 | H | Me | Me | $CH_2N(CH_2CH_2OCONHMe)_2$ | 120d | $C_{25}H_{29}N_3O_8.HCl$ |
| IXa-5 | H | Me | Me | $CH_2NHEt$ | 254–255d | $C_{19}H_{19}NO_4.HCl.H_2O$ |
| IXa-6 | H | Me | Me | $CH_2NHCH_2CH_2OH$ | 251–252d | $C_{19}H_{19}NO_5.HCl$ |
| IXa-7 | H | Me | Me | $CH_2NHCH_2CH_2Cl^d$ | 208–209d | $C_{19}H_{18}ClNO_4$ |
| IXb-1 | OMe | Me | Me | $CH_2NEt_2$ | 222–223d | $C_{22}H_{25}NO_5.HCl$ |
| IXb-2 | OMe | Me | Me | $CH_2N(CH_2CH_2OH)_2$ | 225–227d | $C_{22}H_{25}NO_7.HCl$ |
| IXb-3 | OMe | Me | Me | $CH_2N(CH_2CH_2Cl)_2$ | 200–201d | $C_{22}H_{23}Cl_2NO_5.HCl$ |
| IXb-5 | OMe | Me | Me | $CH_2NHEt$ | 267–269d | $C_{20}H_{21}NO_5.HCl$ |
| IXb-6 | OMe | Me | Me | $CH_2NHCH_2CH_2OH$ | 252–253d | $C_{20}H_{21}NO_6.HCl$ |
| IXb-7 | OMe | Me | Me | $CH_2NHCH_2CH_2Cl.HCl.DMF$ | 204–205d | $C_{20}H_{20}ClNO_5.HCl.C_3H_7NO$ |
| Xa-1 | H | H or Me | Me or H | $CH_2NEt_2$ | 225–227d | $C_{20}H_{21}NO_4.HBr$ |
| Xa-2 | H | H or Me | Me or H | $CH_2N(CH_2CH_2OH)_2$ | 209–216d | $C_{20}H_{21}NO_6.HCl$ |
| Xa-3 | H | H or Me | Me or H | $CH_2N(CH_2CH_2Cl)_2$ | 203–205d | $C_{20}H_{19}Cl_2NO_4.HCl$ |
| Xa-4 | H | H or Me | Me or H | $CH_2N(CH_2CH_2OCONHMe)_2$ | 178–182d | $C_{24}H_{27}N_3O_8.HCl$ |
| Xb-1 | OMe | H or Me | Me or H | $CH_2NEt_2$ | 110–112 | $C_{21}H_{23}NO_5$ |
| Xb-2 | OMe | H or Me | Me or H | $CH_2N(CH_2CH_2OH)_2$ | 221–223 | $C_{21}H_{23}NO_7.HCl$ |
| Xb-3 | OMe | H or Me | Me or H | $CH_2N(CH_2CH_2Cl)_2$ | 152–154 | $C_{21}H_{21}Cl_2NO_5$ |

TABLE III-continued
Synthetic Derivatives of Chrysophanol and Emodin

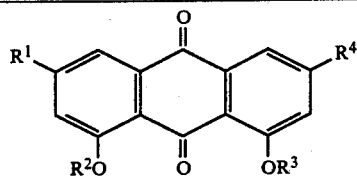

| compd[a] | R[1] | R[2] | R[3] | R[4] | mp, °C.[b,c] | formula |
|---|---|---|---|---|---|---|
| XIa-1 | H | H | H | $CH_2NEt_2$ | 235–238d | $C_{19}H_{19}NO_4 \cdot HCl \cdot \frac{1}{2}H_2O$ |
| XIa-2 | H | H | H | $CH_2N(CH_2CH_2OH)_2$ | 204–207d | $C_{19}H_{19}NO_6 \cdot HCl$ |
| XIa-3 | H | H | H | $CH_2N(CH_2CH_2Cl)_2$ | 211–214d | $C_{19}H_{17}Cl_2NO_4 \cdot HCl$ |
| XIa-4 | H | H | H | $CH_2N(CH_2CH_2OCONHMe)_2$ | 125–131 | $C_{23}H_{25}N_3O_8 \cdot HCl$ |
| XIa-5 | H | H | H | $CH_2NEt$ | >275 | $C_{17}H_{15}NO_4 \cdot HCl$ |
| XIa-6 | H | H | H | $CH_2NHCH_2CH_2OH$ | 255–261d | $C_{17}H_{15}NO_6 \cdot HCl$ |
| XIa-7 | H | H | H | $CH_2NHCH_2CH_2Cl$[d] | 255–261d | $C_{17}H_{14}ClNO_4 \cdot HCl$ |
| XIa-8 | H | H | H | $CH_2NH_2$ | 240–245d | $C_{15}H_{11}NO_4 \cdot HCl \cdot H_2O$ |
| XIa-9 | H | H | H | $CH_2NMe_2$ | 282–283d | $C_{17}H_{15}NO_4 \cdot HCl$ |
| XIa-10 | H | H | H | $CH_2NH(CH_2)_3Me$ | >275 | $C_{19}H_{19}NO_4 \cdot HCl$ |
| XIa-11 | H | H | H | $CH_2NHCH_2CH_2OH$ | 251–252d | $C_{18}H_{17}NO_5 \cdot HCl$ |
| XIa-12 | H | H | H | $CH_2N(CH_2CH_2OCONH\text{-}iPr)_2$ | 159–160 | $C_{27}H_{33}N_3O_8 \cdot HCl$ |
| XIa-13 | H | H | H | $CH_2N(CH_2)_4$ | 255–257d | $C_{19}H_{17}NO_4 \cdot HCl$ |
| XIa-14 | H | H | H | $CH_2N(CH_2)_5$ | 246–247d | $C_{20}H19NO_4 \cdot HCl$ |
| XIa-15 | H | H | H | $CH_2(\text{imidazol-1-yl})$ | 270–272d | $C_{18}H_{12}N_2O_4 \cdot HCl \cdot H_2O$ |
| XIb-1 | OMe | H | H | $CH_2NEt_2$ | 240–241d | $C_{20}H_{21}NO_5 \cdot HBr$ |
| XIb-2 | OMe | H | H | $CH_2N(CH_2CH_2OH)_2$ | 225–227d | $C_{20}H_{21}NO_7 \cdot HCl$ |
| XIb-3 | OMe | H | H | $CH_2N(CH_2CH_2Cl)_2$ | 203–206d | $C_{20}H_{19}Cl_2NO_5 \cdot HCl$ |
| XIb-5 | OMe | H | H | $CH_2NHEt$ | >275 | $C_{18}H_{17}NO_5 \cdot HBr$ |
| XIb-6 | OMe | H | H | $CH_2NHCH_2CH_2OH$ | 259–260d | $C_{18}H_{17}NO_6 \cdot HCl$ |
| XIb-7 | OMe | H | H | $CH_2NHCH_2CH_2Cl$ | powder | $C_{18}H_{16}ClNO_5$ |

[a] All the compounds were analyzed for C, H, X (Br or Cl), and/or N. Analyses for these elements were within ±0.4% of the theoretical values required unless specified otherwise.
[b] For nitrogen-containing compounds, melting points were of the HX salt.
[c] d = decomposition.
[d] Unstable, and satisfactory analyses could not be obtained.

The methyl protecting groups at 1 and 8 could be removed stepwise at various stages (FIG. 1). Thus, treatment of IX with HBr in acetic acid at room temperature afforded a crystalline mixture of 1-O-methyl-8-hydroxy- and 8-O-methyl-1-hydroxy- anthraquinones X, whereas acid hydrolysis at reflux temperature for a few hours resulted in complete demethylation, giving rise to XI. Later, it was found that partially methylated chrysophanol and emodin could be directly brominated to the corresponding mixtures of the monobromides V (major products) and dibromides VII. The former were treated with amines to give X, which were further converted to the corresponding XI. Alternatively, the 3-[(alkylamino)methyl] derivatives XI were prepared by amination of VI. Chlorination of XIa-2 with thionyl chloride afforded XIa-3. N-Methyl- and N-isopropyl-carbamates, XIa-4 and XIa-12, respectively, were prepared by treatment of XIa-2 with the corresponding N-alkyl isocyanates.

SPECTROPHOTOMETRIC STUDIES FOR DNA INTERACTIONS

Some representative compounds were studied for their ability to interact with nucleic acids in solution by comparison of the electronic spectrum of drug alone with that of the drug in the presence of an excess of nucleic acid. All drugs studied have an absorption band in the visible region, separate from the absorption band of the nucleic acids, and therefore any changes in band intensity and position were indicative of drug chromophore-DNA interaction. It was observed that both chrysophanol (Ia) and emodin (Ib) and their derivatives lacking the basic center do not appear to interact with DNA to any significant extent. Since these compounds have low solubility in aqueous solutions, the spectral measurement alone may not be sufficient however to allow one to draw a definite conclusion.

Generally, those anthraquinones bearing an amino function (e.g., Xa-1, Xb-1, XIa-1, Xla-2, XIb-2, and XIb-6) interact with both native and thermally denatured DNA but more strongly with native DNA (FIG. 2). As expected, 1-8-di-O-methylchrysophanol and 1,6,8-tri-O-methylemodin analogues IXa and IXb do not interact with DNA. Anthraquinones wherein one peri-hydroxyl group is methylated (e.g., Xa-2 and Xb-2) interact with DNA to a lesser extent than the corresponding unmethylated (XIa-2 and XIb-2). It is interesting to note that while DNA induced changes in absorption spectra of some derivatives (e.g., XIa-7 and XIb-7), these do not appear to connected with the alklating capabilities in view of the fact that they could be reversed by addition of $Me_2SO$ (to 1:1 v/v). The dissociation of nonbonded ligand-DNA complexes in the presence of organic solvents is a phenomenon well documented. (Wakelin, L. P. G., et al., Biochemistry 20:5779 (1981)).

Changes in the absorption spectra of the drugs (FIG. 2) are not inconsistent with the possiblity of the intercalative mode of binding. Other types of nonbinding interactions, however, (e.g. binding to the minor groove of the double helix (Bloomfield, V. A., et al., In Physical Chemistry of Nucleic Acids; Harper and Row: New York, pp. 432–434 (1974); Jorgenson, K. F., et al., J. Biomol. Struct. Dyn. 6:1005 (1988)) cannot be excluded. It is well-known that intercalative binding, which most often has an ionic component, is affected by a rise in concentration of salts, (Kapuscinski, J., Darzynkiewicz, Z. J., Biomol. Struct. Dyn. 5:127 (1987), and compounds such as Xa-2, Xb-2, XIb-3, and XIb-7 lost the ability to interact with DNA when Na. concentration was increased from 0.01 to 0.1 M. On the basis of this fact one can conclude that the affinity for DNA of these compounds is lower than those that interact with DNA at both ionic strengths.

No straightforward correlation is apparent between the DNA-affinity data of the drugs studied and their biological activity.

BIOLOGICAL ACTIVITIES

Preliminary biological data for inhibiting cell growth of murine L1210 leukemic cells and human acute promyelocytic leukemia cells (HL-60) during 72 h of exposure to the compounds are given in Table IV. The potencies for inhibiting [$^3$H]TdR incorporation into DNA in HL-60 cells during the initial 30-min period are also given in Table IV. It is interesting to note that 1,8-di-O-methyl derivatives are uniformly devoid of activity against L1210 leukemic cells. These results are consistent with published data that compare the ratios of the potencies (ID$_{50}$'s) for cell growth inhibition (A) and inhibition of [$^3$H]TdR incorporation into DNA in HL-60 cells (B). The B/A ratios allow an indirect estimation of whether or not cytotoxicities exerted by these analogues are primarily due to initial inhibition of DNA synthesis. The B/A ratios for Vb, VIIa, VIIb, VIIIb, Xa-3, and XIa-3 are 41, 217, 237, 579, 39, and 383, respectively, suggesting that these compounds exert their initial effects mainly on processes other than DNA synthesis per se (Table V). These results suggest that these compounds exert their cytotoxic effects in a time-dependent manner and their initial action is targeted at the sites other than DNA elongation. Whether these analogues, like m-AMSA, ellipticine, or anthracyclines, act by inhibiting DNA topoisomerase II remains to be explored. It is of interest to note that the above-mentioned anthraquinones are among the most potent anti-leukemic analogues listed in Table IV, with ID$_{50}$ values ranging from $1.4 \times 10^6$ to $4.2 \times 10^{11}$ for L1210$^{48}$ cells and $1.7 \times 10^6$ to $6.0 \times 10^8$ M for HL-60 cells. Our preliminary experiments indicate that the compounds arrest cells in the S and/or G$_2$ phases of the cell cycle (unpublished results).

TABLE IV

Biological Activities of Derivatives of Chrysophanol and Emodin

| compd | ID$_{50}$, M (L1210 cell growth) | ID$_{50}$, M [HL-60 cell growth (72 h)] (A) | ID$_{50}$, M (HL-60 TdR into DNA (B) | B/A |
|---|---|---|---|---|
| IIa | $2.8 \times 10^{-5}$ | $1.0 \times 10^{-5}$ | $1.9 \times 10^{-5}$ | 1.9 |
| IIb | $1.0 \times 10^{-4}$ | $4.9 \times 10^{-5}$ | $2.1 \times 10^{-5}$ | 0.43 |
| IIIa | $9.2 \times 10^{-6}$ | $4.4 \times 10^{-6}$ | $1.1 \times 10^{-5}$ | 2.5 |
| IIIb | $6.8 \times 10^{-7}$ | $8.4 \times 10^{-5}$ | $1.2 \times 10^{-5}$ | 0.14 |
| IVa | $8.9 \times 10^{-7}$ | $2.1 \times 10^{-6}$ | $9.0 \times 10^{-6}$ | 4.3 |
| IVb | $4.1 \times 10^{-5}$ | $6.0 \times 10^{-6}$ | $5.8 \times 10^{-5}$ | 9.7 |
| Va | $8.8 \times 10^{-6}$ | $7.1 \times 10^{-6}$ | $1.2 \times 10^{-5}$ | 1.7 |
| Vb | $6.8 \times 10^{-8}$ | $1.7 \times 10^{-6}$ | $7.0 \times 10^{-5}$ | 41 |
| VIa | $8.6 \times 10^{-6}$ | $7.1 \times 10^{-6}$ | $1.6 \times 10^{-5}$ | 2.3 |
| VIb | $5.9 \times 10^{-5}$ | $2.5 \times 10^{-5}$ | $3.4 \times 10^{-4}$ | 13.6 |
| VIIa | $4.2 \times 10^{-11}$ | $6.0 \times 10^{-8}$ | $1.3 \times 10^{-5}$ | 217 |
| VIIb | $1.0 \times 10^{-9}$ | $9.7 \times 10^{-8}$ | $2.3 \times 10^{-5}$ | 237 |
| VIIIa | $4.4 \times 10^{-7}$ | $2.5 \times 10^{-6}$ | $3.9 \times 10^{-5}$ | 15.6 |
| VIIIb | $1.0 \times 10^{-9}$ | $1.9 \times 10^{-7}$ | $1.1 \times 10^{-4}$ | 579 |
| IXa-1 | $1.3 \times 10^{-4}$ | $3.0 \times 10^{-5}$ | $1.9 \times 10^{-5}$ | 6.3 |
| IXa-2 | $>5.0 \times 10^{-5}$ | $4.9 \times 10^{-4}$ | $1.4 \times 10^{-5}$ | 0.03 |
| IXa-3 | $1.3 \times 10^{-5}$ | $1.8 \times 10^{-4}$ | $1.4 \times 10^{-5}$ | 7.8 |
| IXa-4 | $7.2 \times 10^{-5}$ | $9.5 \times 10^{-5}$ | $9.4 \times 10^{-6}$ | 0.99 |
| IXa-5 | $1.2 \times 10^{-6}$ | $4.8 \times 10^{-5}$ | $2.9 \times 10^{-5}$ | 0.60 |
| IXa-6 | $1.4 \times 10^{-4}$ | $5.5 \times 10^{-5}$ | $4.6 \times 10^{-5}$ | 0.84 |
| IXa-7 | $2.6 \times 10^{-5}$ | $8.6 \times 10^{-5}$ | $1.9 \times 10^{-5}$ | 0.22 |
| IXb-1 | $6.9 \times 10^{-6}$ | $7.9 \times 10^{-6}$ | $4.2 \times 10^{-6}$ | 0.53 |
| IXb-2 | $>2.7 \times 10^{-5}$ | $1.0 \times 10^{-4}$ | $1.7 \times 10^{-5}$ | 0.17 |
| IXb-3 | $2.7 \times 10^{-6}$ | $2.0 \times 10^{-6}$ | $8.9 \times 10^{-6}$ | 4.5 |
| IXb-5 | $9.8 \times 10^{-6}$ | $1.7 \times 10^{-5}$ | $1.3 \times 10^{-5}$ | 0.76 |
| IXb-6 | $1.7 \times 10^{-5}$ | $1.1 \times 10^{-4}$ | $2.6 \times 10^{-5}$ | 0.24 |
| IXb-7 | $3.2 \times 10^{-6}$ | $5.8 \times 10^{-6}$ | $1.8 \times 10^{-5}$ | 3.1 |
| Xa-1 | $1.2 \times 10^{-5}$ | $5.2 \times 10^{-6}$ | $1.4 \times 10^{-5}$ | 2.7 |
| Xa-2 | $>2.4 \times 10^{-5}$ | $2.1 \times 10^{-5}$ | $8.9 \times 10^{-5}$ | 4.2 |
| Xa-3 | $1.4 \times 10^{-6}$ | $3.9 \times 10^{-7}$ | $1.5 \times 10^{-5}$ | 38.5 |
| Xa-4 | $8.9 \times 10^{-5}$ | $1.2 \times 10^{-5}$ | $1.2 \times 10^{-5}$ | 1 |
| Xb-1 | $6.9 \times 10^{-6}$ | $6.7 \times 10^{-6}$ | $1.8 \times 10^{-4}$ | 26.9 |
| Xb-2 | $8.8 \times 10^{-6}$ | $>5.0 \times 10^{-4}$ | $9.6 \times 10^{-6}$ | 0.02 |
| Xb-3 | $3.3 \times 10^{-6}$ | $5.2 \times 10^{-7}$ | $5.4 \times 10^{-4}$ | 10.4 |
| XIa-1 | $2.8 \times 10^{-6}$ | $1.8 \times 10^{-6}$ | $1.4 \times 10^{-5}$ | 7.8 |
| XIa-2 | $5.9 \times 10^{-6}$ | $3.3 \times 10^{-6}$ | $1.4 \times 10^{-5}$ | 4.2 |
| XIa-3 | $1.3 \times 10^{-7}$ | $1.8 \times 10^{-7}$ | $6.9 \times 10^{-5}$ | 383 |
| XIa-4 | $>1.8 \times 10^{-5}$ | $2.1 \times 10^{-4}$ | $2.8 \times 10^{-5}$ | 0.13 |
| XIa-5 | $7.7 \times 10^{-7}$ | $8.7 \times 10^{-6}$ | $1.8 \times 10^{-5}$ | 2.1 |
| XIa-6 | $1.6 \times 10^{-7}$ | $8.6 \times 10^{-7}$ | $1.5 \times 10^{-5}$ | 17.4 |
| XIa-7 | $7.1 \times 10^{-6}$ | $7.5 \times 10^{-6}$ | $3.9 \times 10^{-5}$ | 5.2 |
| XIa-8 | $8.5 \times 10^{-6}$ | $1.1 \times 10^{-5}$ | $2.5 \times 10^{-5}$ | 2.3 |
| XIa-9 | $2.2 \times 10^{-6}$ | $2.7 \times 10^{-6}$ | $9.3 \times 10^{-6}$ | 3.3 |
| XIa-10 | $4.6 \times 10^{-6}$ | $4.1 \times 10^{-6}$ | $2.5 \times 10^{-5}$ | 6.1 |
| XIa-11 | $6.7 \times 10^{-7}$ | $3.2 \times 10^{-6}$ | $1.6 \times 10^{-5}$ | 5.0 |
| XIa-12 | $2.7 \times 10^{-5}$ | $2.7 \times 10^{-5}$ | $1.7 \times 10^{-5}$ | 0.63 |
| XIa-13 | $1.6 \times 10^{-6}$ | $2.1 \times 10^{-6}$ | $1.0 \times 10^{-5}$ | 4.8 |
| XIa-14 | $4.0 \times 10^{-6}$ | $2.8 \times 10^{-6}$ | $6.3 \times 10^{-5}$ | 22.5 |
| XIa-15 | $7.4 \times 10^{-6}$ | $4.8 \times 10^{-6}$ | $4.3 \times 10^{-5}$ | 9.0 |
| XIb-1 | $1.2 \times 10^{-6}$ | $3.4 \times 10^{-6}$ | $3.5 \times 10^{-5}$ | 10.3 |
| XIb-2 | $1.4 \times 10^{-5}$ | $6.6 \times 10^{-6}$ | $4.5 \times 10^{-5}$ | 5.2 |
| XIb-3 | $2.3 \times 10^{-8}$ | $6.1 \times 10^{-7}$ | $1.2 \times 10^{-5}$ | 19.7 |
| XIb-5 | $7.2 \times 10^{-7}$ | $2.1 \times 10^{-6}$ | $1.3 \times 10^{-5}$ | 6.2 |
| XIb-6 | $5.0 \times 10^{-7}$ | $1.6 \times 10^{-6}$ | $1.2 \times 10^{-5}$ | 7.5 |
| XIb-7 | $1.8 \times 10^{-5}$ | $9.2 \times 10^{-6}$ | $2.2 \times 10^{-4}$ | 23.9 |

TABLE V

Inverse Relationship Between Cell Growth Inhibition and Inhibition of Initial Thymidine Incorporation Into DNA in HL-60 Cells by Chrysophanol Derivatives$^a$

| no. of compds. examined | value of IC$_{50}$ (cell growth), μM range | mean ± SE | ratio of IC$_{50}$ (dThd incorpn)/IC$_{50}$ (cell growth), mean ± SE |
|---|---|---|---|
| 8 | <1 | 0.36 ± 0.10 | 167.3 ± 72.4 |
| 17 | 1–5 | 2.73 ± 0.24 | 9.55 ± 2.30 |
| 15 | 5–10 | 7.42 ± 0.53 | 6.32 ± 2.10 |
| 7 | 10–50 | 28.43 ± 5.51 | 3.03 ± 1.83 |
| 8 | >50 | 204.4 ± 65.4 | 0.22 ± 0.09 |

$^a$Cell growth inhibition was measured at the end of 72-h exposure to each compound as described under Experimental Section. Inhibition of [H$^3$]dThd incorporation into DNA was measured during the first 30 min of exposure to each corresponding compound as described under Experimental Section.

MATERIALS AND METHODS

Melting points were determined on a Thomas-Hoover capillary apparatus and are uncorrected. Elemental analyses were performed by M-H-W Laboratories, Phoenix, Ariz, and all new compounds with the exception of IXa-7 and XIa-7, which were unstable, analyzed correctly. $^1$H NMR spectra were recorded on a JOEL FX90Q spectrometer with Me$_4$Si as the internal standard. Chrysophanol (Ia) and emodin (Ib) were isolated form rhubarb extract by the procedure of Kelly et al. (Kelly, T. R., et al., J. Org. Chem. 48:3578 (1983)) except CH$_2$Cl$_2$ was used instead of Et$_2$O throughout the isolation process.

The following examples are illustrative of the process and products of the present invention, but are not to be construed as limiting.

EXAMPLE 5

1,8-Dimethoxy-3-methyl-9,10-anthraquinone (1,8-Di-O-methylchrysophanol, IIa)

A mixture of chrysophanol (Ia, 7.0 g, 0.029 mol), $K_2CO_3$ (10 g, 0.071 mol), and $Me_2SO_4$ (10 mL, 0.1 mol) in $Me_2CO$ (300 mL) was stirred under reflux for 16 h and then concentrated in vacuo. The residue was triturated well with water (300 mL), and the crystalline IIa (7.5 g, 96%) was collected by filtration and air-dried: mp 191–193° C. (lit, (Beilstein, 8:473) mp 195° C.); $^1H$ NMR $(CDCl_3)\delta 2.46$ (3 H, s, 3-Me), 3.98 (3 H, s, OMe), 3.99 (3 H, s, OMe), 7.08–7.86 (5 H, m, H-2,4,5,6,7). Anal. $(C_{17}H_{14}O_4)$ C, H.

EXAMPLE 6

1,3,8-Trimethoxy-6-methyl-9,10-anthraquinone (1,3,8-Tri-O-methylemodin, IIb)

In a similar manner, emodin (Ib, 1.0 g, 3.9 mmol) was converted into IIb (1.04 g, 90%): mp 225° C. (lit. (Beilstein, 8:523) mp 225° C.); $^1H$ NMR $(Me_2SO-d_6)\delta 2.43$ (3 H, s, 6-Me) 3.88 (3 H, s, OME), 3.92 (6 H, s, 2×OMe), 6.94 (1 H, d, H-7, $J_{5,7}=2.2$ Hz), 7.13 (1 H, d, H-5, $J_{-5,7}=2.2$ Hz), 7.33 (1 H, s, H-2), 7.46 (1 H, s, H-4). Anal. $(C_{18}H_{16}BrO_5)$ C, H.

EXAMPLE 7

6-(Dibromomethyl)-1,3,8-trimethoxy-9,10-anthraquinone (IVb)

In a similar manner, IIb (3.12 g, 0.01 mol) was brominated to give IIIb (3.06 g, 74.4%) [mp 250–254° C.; (lit. Alexander, J., et al., J. Org. Chem. 45:20 (1980)) mp. 233.5–234 degrees C); $^1H$ NMR $(CDCl_3)$ was identical with that reported (Alexander, J., et al.)] and IVb (197 mg) [mp 254–257 degrees C; 1H NMR $(CDCl_3)$ delta 3.95 (6 H, s, 2 X OMe), 3.97 (3 H, s, OMe), 6.67 (1 H, s, $CHBr_2$), 6.78 (1 H, d, H-7, $J_{5,7}=2.47$ Hz), 7.32 (1 H, d, H-5), 7.54 (1 H, d, H-2, $J_{2,4}=1.92$ HZ), 7.90 (1 H, d, H-4)]. Anal. $(C_{17}H_{14}Br_2O_5)$ C, H, Br.

EXAMPLE 8

3-(Bromomethyl)-1(and 8)-Hydroxy-8(and 1)-Methoxy-9,10-anthraquinone (Va)

A mixture of IIIa (70 mg, 0.19 mmol in HOAc (10 mL) and 30% HBr/HOAc (1 mL) was stirred overnight at room temperature and then concentrated in vacuo. The residue was chromatographed on a silica gel column using $CHCl_3$ as the eluent to give 51 mg (76%) of Va as yellow crystals: mp 213–215° C.; 1H NMR $(CDCl_3)\delta 4.08$, 4.10 (2×3 H, 2 s, 1- and 8-OMe), 4.47, 4.54 (2×2 h, 2 s, $CH_2Br$), 7.24–8.04 (10 H, m, H-2,4,5,6,7). Anal. $(C_{16}H_{11}BrO_4)$ C, H, Br.

EXAMPLE 9

3-(Dibromomethyl)-1(and 8)-hydroxy-8(and 1)-methoxy-9,10anthraquinone (VIIa) and 6-(Dibromomethyl)-1-(and 8)-hydroxy-3,8(and 1,3)-dimethoxy-9,10-anthraquinone (VIIb)

In a similar manner, from IVa (200 mg, 0.453 mmol) and IVb (100 mg, 0.213 mmol), VIIa (82 mg, 42.5%) and VIIb (82 mg., 84.4%), respectively, were prepared (see Table III).

EXAMPLE 10

3-(Dibromomethyl)-1,8-dihydroxy-9,10-anthraquinone (VIIIa) and 6-(Dibromomethyl)-3-methoxy-1,8-dihydroxy-9,10-anthraquinone (VIIIb)

In a similar manner, IVa (237 mg, 0.54 mmol) and IVb (472 mg, 1 mmol) were converted into VIIIa (166 mg, 75%) and VIIIb (408 mg, 95%), respectively (Table III).

EXAMPLE 11

3-[(Diethylamino)methyl]-1,8-dimethoxy-9,10-anthraquinone (IXa-1)

To a solution of IIIa (200 mg, 0.55 mmol) in (10.0 mL) was added $Et_2NH$ (5.0 mL), and the mixture was stirred at room temperature for 3 days. The mixture was partitioned between EtOAc (20 mL) and $H_2O$ (20 mL). The aqueous layer was washed with EtOAc (20 mL). The combined EtOAc solutions were washed with $H_2O$ (2×20 mL) and saturated NaCl (2×20 mL), dried ($Na_2SO_4$), and concentrated, and the residue was chromatographed on a silica gel column first with $CHCl_3$, which eluted the 3-(hydroxymethyl) derivative (33 mg), followed by $CHCl_3$ containing 3% MeOH. The IXa (140 mg) that eluted from the column was converted to the crystalline HCl salt (142 mg, 63%), mp 154–158° C.

In a similar manner but by using the corresponding amines, IXa-2, -5, and -6, were prepared (Table III). Also by use of the same procedure starting from IIIb and the corresponding amines, IXb-1, -2, -5, and -7 were synthesized (Table III).

EXAMPLE 12

3-[(Diethylamino)methyl]-(or 8)-hydroxy-8(or 1)-methoxy-9,10-anthraquinone (Xa-1)

The HCl salt monohydrate of IXa (100 mg, 0.25 mmol) was dissolved in a mixture of HOAc (5 mL) and 30% HBr/HOAc (0.4 mL), and the solution was stirred at room temperature for 24 h. After concentration in vacuo, the residue was partitioned between saturated $NaHCO_3$ (10 mL) and $CHCl_3$ (10 ml). The $ChCl^3$ layer was dried ($Na_2SO_4$) and concentrated and the residue chromatographed on a silica gel column using $CHCl_3$-MeOH (30:1 v/v) to give Xa-1 as a glass, which was dissolved in 1 N HBr (1 mL). Upon dilution of the solution with EtOH (5 mL), the monohydrobromide of Xa-1 (82 mg) precipitated as yellow microcrystals, mp 225–227° C. dec.

In a similar manner, Xa-2-4 and Xb 1-4 were prepared (Table III).

SPECTRAL STUDIES

Absorption spectra were measured with an IBM 9410 UV-visible spectrometer interfaced to an HP 9826 computer. Small volumes of the stock drug solutions (2 mg/mL in $Me_2SO$) were added to 2 mL of buffer (0.01 or 0.1 M NaCl, 5 mM Hepes, pH 7) to obtain a final drug concentration of 5–15 $\mu M$, or to the solution of native or thermally denatured DNA (0.2 and 0.1 mM, respectively) in the buffer. After incubation at room temperature for 10 min, the spectra were recorded in the 300–600 nm range (increment 1 nm) and corrected by subtracting the spectrum of the blank which was measured before addition of the drug.

BIOLOGICAL ASSAYS

Method A

For cell growth inhibition studies, HL-60 cells 92.0×10⁵/mL) were grown in RPMI 1640 media at 37° C. in humidified 5% $CO_2$ for 72 h. Viable cells were counted with the trypan blue exclusion method. The fractional inhibitions at four or five concentrations of compounds (in 0.2% DMSO) were analyzed with a median-effect plot (Chou, T.-C., et al., Adv. Enzyme Regul. 22:27 (1984)) by using a computer program. (Chou, J.; Chou, T.-C. Dose-Effect Analyses with Microcomputer. Quantitation of $ID_{50}$, $LD_{50}$, Synergism, Antagonism, Low-dose Risk, Receptor-Binding and Enzyme Kinetics; IBM-PC Series, Elsevier-Biosoft, Elsevier Scientific: Cambridge, U.K., (1986)). The median-effect concentration ($ID_{50}$) was automatically determined for the x intercept of the median-effect plot. Cell growth in the absence of a compound and in the presence of DMSO was used as a control. DMSO (0.2%) alone inhibited cell growth 3.8±1.2% during the 72-h incubation period.

Method B

For precursor incorporation studies, each compound at four to six concentrations (0.2% DMSO) was preincubated with HL-60 cells (2.5×10⁶/Ml) for 15 min prior to the addition of [³H-methyl]TdR (1 μCi, 0.15 nmol/mL) and was incubated for 30 min. The incubation conditions and the procedures for isolating the DNA fractions were described previously (Chou, T.-C, et al., J. Cancer Res. 43:3074 (1983)). The incorporation of radioactivity in DNA in the absence of an analogue in the presence of DMSO was used as a control. The control value for incorporation into DNA was 8500±300 cpm/10⁶ cells.

EXPERIMENT 3

This experiment concerns Topoisomerase II (Topo II)-mediated DNA cleavage activity induced by chrysophanol derivatives. 3-(bis[2-chloroethyl]amino)-methyl-1,8-dihydroxy-9,10-anthraquinone (SK-31662) and 3-(2-hydroxyethylamino)methyl-1,8-dihydroxy-9,10-anthraquinone (SK-31694) have antileukemic activity with IC>es of 0.14 and 0.86 uM, respectively. SK-31662 and SK-31694 inhibit kDNA decatenation at 48 and 38 uM, respectively. The mapping of DNA-Topo II cleavage sites using Hind III-digested 3'-labeled DNA and nuclear extracts (NE) of HL-60 cells showed that at 10 uM these two agents induce protein-linked DNA breaks with a cleavage site pattern similar to m-AMSA. They also stimulate the formation of Topo II cleavable complex in the presence of 3'-labeled DNA and NE. The amounts of protein-linked DNA induced by VP-16 and SK-31694 are reduced during 0.5 min exposure to 65 degrees C whereas SK-31662-induced protein-linked DNA complex cannot be reversed up to 15 min. The data suggest that Topo II appears to be a major cytotoxic target for these compounds and DNA intercalator with alkylating groups interact with Topo II system in an irreversible manner with enhanced toxicity.

What is claimed is:

1. A method which comprises administering to a subject an amount of a compound having the structure:

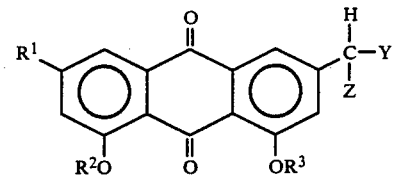

wherein
$R^1$ is hydrogen, a hydroxy group or a methoxy group;
$R^2$ is hydrogen or a methyl group;
$R^3$ is hydrogen or a methyl group;
Y is a secondary amino group (NHalkyl) or a tertiary amino group (N(alkyl)₂); and
Z is hydrogen or a halogen, effective to inhibit topoisomerase II.

2. A method which comprises administering to a subject an amount of a compound having the structure:

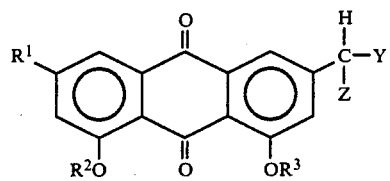

wherein
$R^1$ is hydrogen, a hydroxy group or a methoxy group;
$R^2$ is hydrogen or a methyl group;
$R^3$ is hydrogen or a methyl group;
Y is a halogen, secondary amino group (NHalkyl) or a tertiary amino group (N(alkyl)₂); and
Z is hydrogen or a halogen, effective to inhibit topoisomerase II.

3. A method of claim 2, wherein the halogen is chlorine or bromine.

4. A method of claim 2, wherein the secondary amino group comprises a lower alkyl group or a substituted lower alkyl group where each substituent is a halogen or a hydroxy, benzoxy, or acetyloxy group.

5. A method of claim 2, wherein the tertiary amino group comprises two lower alkyl groups or substituted lower alkyl groups where each substituent is a halogen or a hydroxy, benzoxy, or acetyloxy group and where the lower alkyl groups or the substituted lower alkyl groups are the same or different.

6. A method of claim 2, wherein the compound is selected from the group consisting of:
3-(N,N-diethylamino)methyl-1,8-dihydroxy-9,10-anthraquinone;
3-(N-ethylamino)methyl-1,8-dihydroxy-9,10-anthraquinone;
3-[N,N-bis(2-hydroxyethyl)amino]methyl-1,8-dihydroxy-9,10-anthraquinone;
3-[N-(2-hydroxyethyl)amino]methyl-1,8-dihydroxy-9,10-anthraquinone;
3-(N,N-diethylamino)methyl-1,8-dihydroxy-6-methoxy-9,10-anthraquinone;
3-(N, ethylamino)methyl-1,8-dihydroxy-6-methoxy-9,10-anthraquinone;
3-[N,N-bis(2-hydroxyethyl)amino]methyl-1,8-dihydroxy-6-methoxy-9,10-anthraquinone;
3-[N-(2-hydroxyethyl)amino]methyl-1,8-dihydroxy-6-methoxy-9,10-anthraquinone;

3-(N,N-diethylamino)methyl-1,8-dimethoxy-9,10-anthraquinone;
3-(N,ethylamino)methyl-1,8-dimethoxy-9,10-anthraquinone;
3-[N,N-bis(2-hydroxethyl)amino]methyl-1,8-dimethoxy-9,10-anthraquinone;
3-[N-(2-hydroxyethyl)amino]methyl-1,8-dimethoxy-9,10-anthraquinone;
3-(N,N-diethylamino)methyl-1,6,8-trimethoxy-9,10-anthraquinone;
3-(N-ethylamino)methyl-1,6,8-trimethoxy-9,10-anthraquinone; and
3-[N,N-bis(2-hydroxyethyl)amino]methyl-1,6,8-trimethoxy-9,10-anthraquinone.

7. A method of claim 2, wherein the compound is selected from the group consisting of:
3-[N,N-bis(2-chloroethyl)amino]methyl-1,8-dihydroxy-9,10-anthraquinone;
3-[N-(2-chloroethyl)amino]methyl-1,8-dihydroxy-9,10-anthraquinone;
3-[N,N-bis(2-chloroethyl)amino]methyl-1,8-dihydroxy-6-methoxy-9,10-anthraquinone;
3-[N-(2-chloroethyl)amino]methyl-1,8-dihydroxy-6-methoxy-9,10-anthraquinone;
3-[N,N-bis(2-chloroethyl)amino]methyl-1,8-dimethoxy-9,10-anthraquinone;
3-[N-(2-chloroethyl)amino]methyl-1,8-dimethoxy-9,10-anthraquinone;
3-[N,N-bis(2-chloroethyl)amino]methyl-1,6,8-trimethoxy-9,10-anthraquinone; and
3-[N-(2-chloroethyl)amino]methyl-1,6,8-trimethoxy-9,10-anthraquinone.

8. A method of claim 2, wherein the compound is selected from the group consisting of:
3-bromomethyl-1,8-dihydroxy-9,10-anthraquinone;
3,3-dibromomethyl-1,8-dihydroxy-9,10-anthraquinone;
3-bromomethyl-1,8-dimethoxy-9,10-anthraquinone;
3,3-dibromomethyl-1,8-dimethoxy-9,10-anthraquinone;
3-bromomethyl-1,8-dihydroxy-6-methoxy-9,10-anthraquinone;
3,3-dibromomethyl-1,8-dimethoxy-6-methoxy-9,10-anthraquinone;
3-bromomethyl-1,6,8-trimethoxy-9,10-anthraquinone; and
3,3-dibromomethyl-1,6,8-trimethoxy-9,10-anthraquinone.

* * * * *